United States Patent [19]

Hukuhara

[11] Patent Number: 5,007,296
[45] Date of Patent: Apr. 16, 1991

[54] APPARATUS FOR MEASURING A LIQUID SPECIMEN

[75] Inventor: Takahito Hukuhara, Kakogawashi, Japan

[73] Assignee: 501 Toa Medical Electronics Co., Ltd., Kobe, Japan

[21] Appl. No.: 424,343

[22] Filed: Oct. 19, 1989

[30] Foreign Application Priority Data

Jan. 26, 1989 [JP] Japan .................................. 1-7912

[51] Int. Cl.[5] .......................................... G01N 15/14
[52] U.S. Cl. ................................. 73/864.87; 324/450; 324/71.4; 356/410; 204/409
[58] Field of Search ..................... 324/724, 71.1, 71.4, 324/464, 425, 439, 446, 450, 65 P; 73/864.81–864.87; 204/400, 403, 409; 356/402, 410, 411; 377/12

[56] References Cited

U.S. PATENT DOCUMENTS

| | | | |
|---|---|---|---|
| 3,049,118 | 8/1962 | Arthur et al. | 324/446 X |
| 3,197,644 | 7/1965 | Etzrodt, Jr. et al. | 350/411 |
| 3,361,965 | 1/1968 | Coulter et al. | 324/450 X |
| 3,475,128 | 10/1969 | Thiers | 204/409 X |
| 3,743,424 | 7/1973 | Coulter | 356/410 X |
| 4,103,229 | 7/1978 | Gear | 73/865.5 X |
| 4,172,770 | 10/1979 | Semersky et al. | 204/409 X |
| 4,218,197 | 8/1980 | Meyer et al. | 204/402 X |
| 4,240,438 | 12/1980 | Updike et al. | 204/403 X |
| 4,339,317 | 7/1982 | Meiattini et al. | 204/403 X |
| 4,553,552 | 11/1985 | Valdespino et al. | 128/637 |
| 4,926,702 | 5/1990 | Stephens et al. | 73/863.01 X |
| 4,929,426 | 5/1990 | Bodei et al. | 204/400 X |

FOREIGN PATENT DOCUMENTS 3017774 11/1981 Fed. Rep. of Germany ...... 356/410
32351 2/1987 Japan ................................... 204/403

OTHER PUBLICATIONS

"An Instrument for the Rapid Determination of L-Lactate in Biological Fluids", Medical Instrumentation; vol. 9, No. 1, Jan.-Feb. 1975, pp. 11-14, R. Racine et al., in 204/403.

Primary Examiner—Tom Noland
Attorney, Agent, or Firm—Thomas R. Morrison

[57] ABSTRACT

A particle detector for detecting particles of blood components in an electrolyte employs a minute hole through which a fixed quantity of the material is drawn. Electrodes inside and outside the detector pass an electric current through the minute hole. When a particle passes through the hole, it partially blocks the hole, whereby a sharp change is experienced in the amount of current passing through the electrolyte. A syringe fluid path in the detector enters the fluid path for the test fluid at right angles thereto. The inside electrode is disposed in the syringe fluid path near its junction with the fluid path for the test fluid. A colorimeter is placed in series with the flow of the test fluid to measure the concentration of hemoglobin in the test fluid. Automated control of the particle detector is provided by a plurality of cams driving a corresponding plurality of pistons. One of the pistons serves as a syringe for pumping test fluid during a test and for pumping purge fluid for cleanup prior to the next test. The remaining pistons, with interconnecting chambers, perform valve functions.

7 Claims, 3 Drawing Sheets

FIG. 1
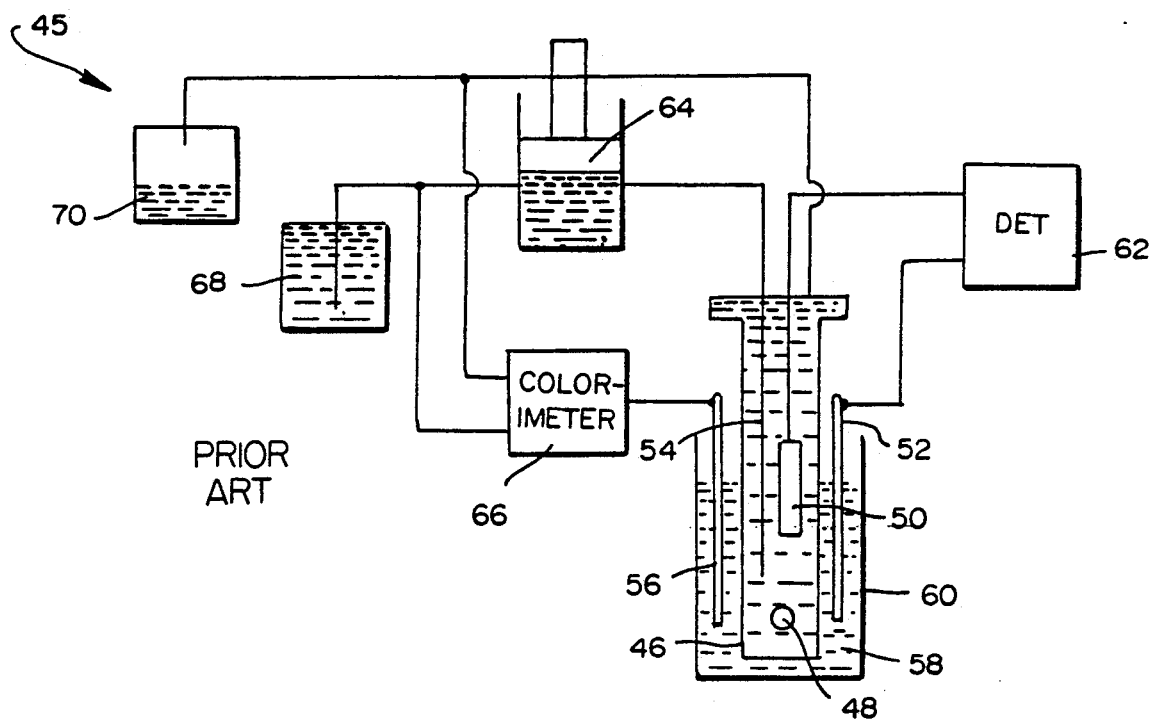
PRIOR ART
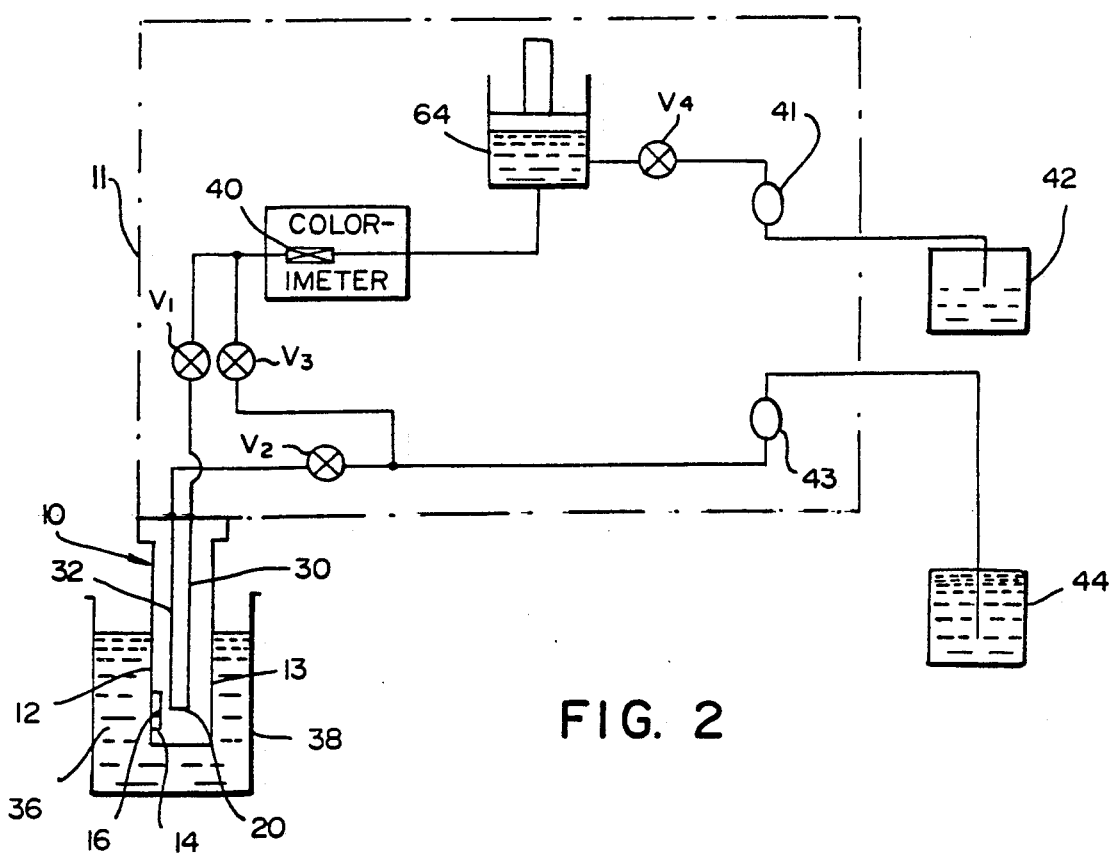
FIG. 2

FIG. 5
FIG. 6
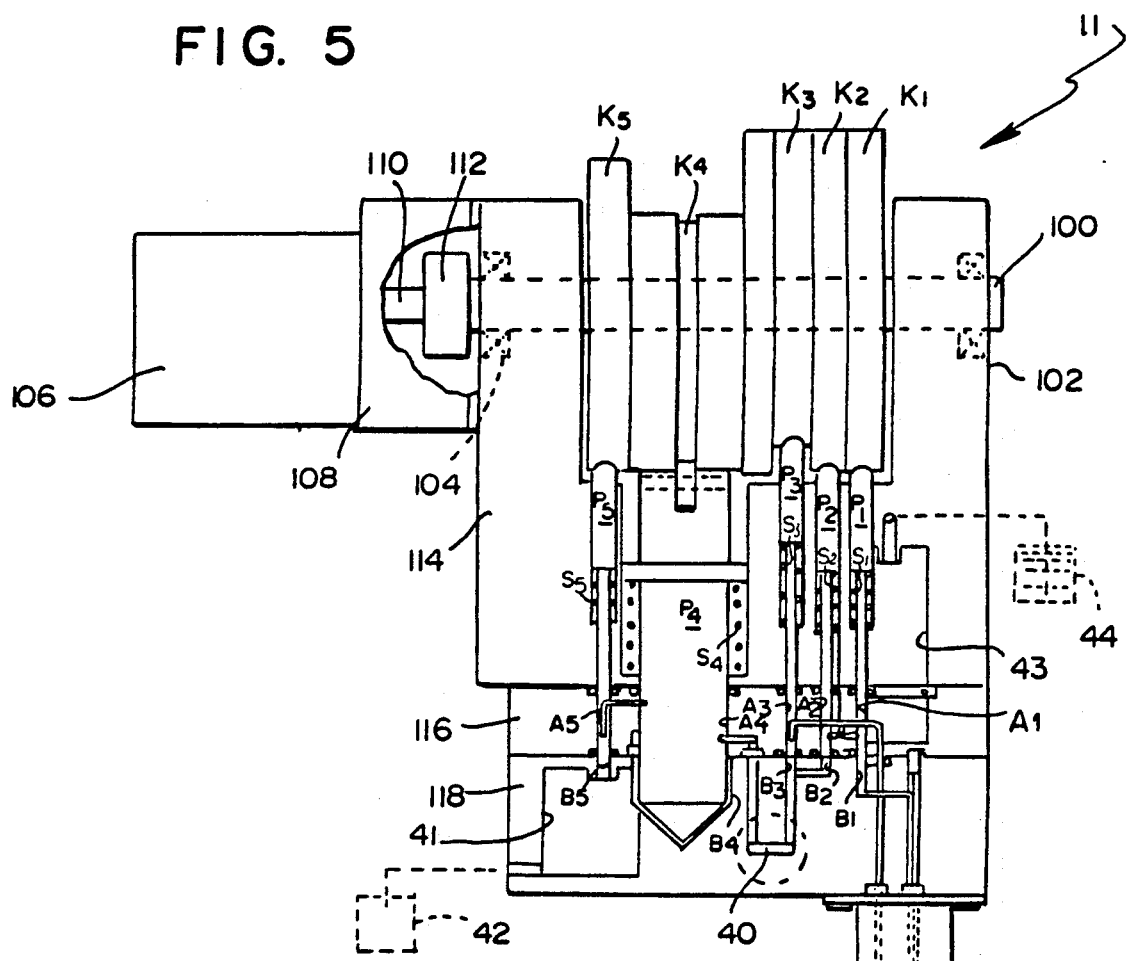
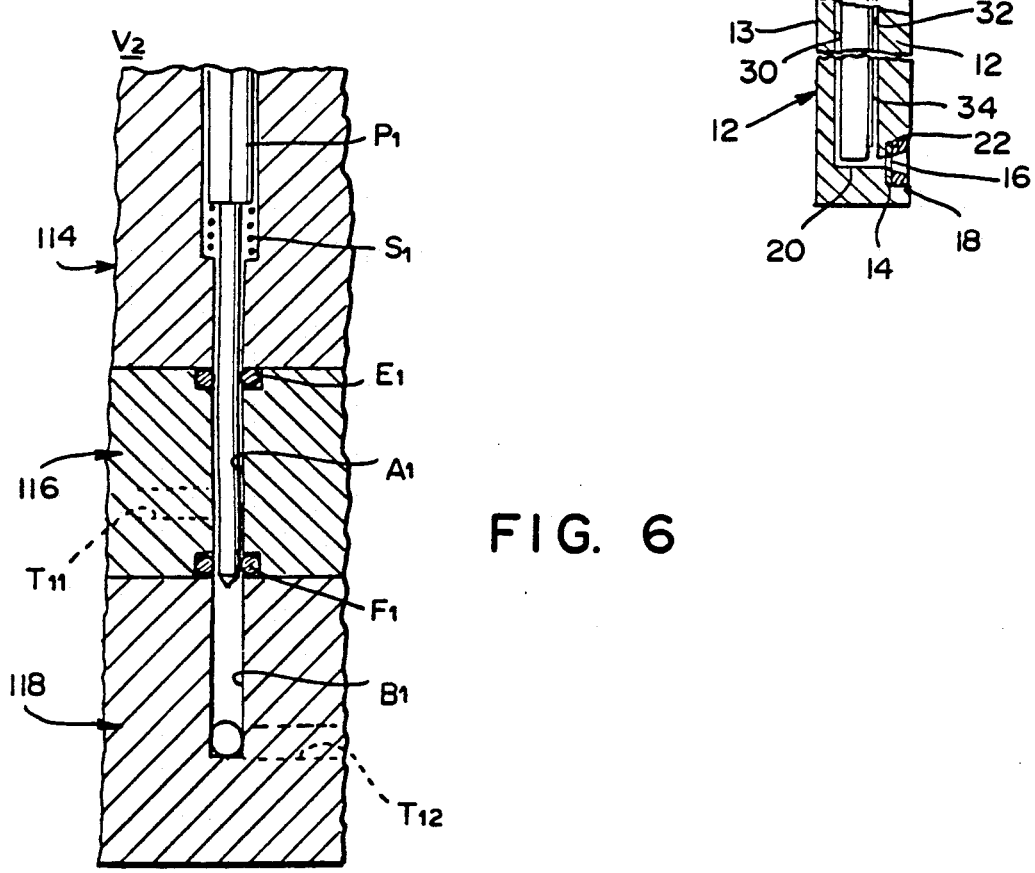

APPARATUS FOR MEASURING A LIQUID SPECIMEN

BACKGROUND OF THE INVENTION

The present invention relates to measuring devices, and more particularly, to apparatus for measuring a test liquid where a number of particles and an amount of pigment are measured.

To measure the number and the size of blood components (leukocytes, corpuscles, etc.) in a blood sample, the prior art mixes the blood sample with an electrically conducting liquid, and passes a fixed volume of the mixture through a minute hole. Electrodes on opposed sides of the minute hole pass an electric current through the mixture, and particularly through the hole. The electrical resistance of blood components is different from that of the electrolyte. As a result, when a particle of blood component passes through the minute hole, it partly blocks the minute hole, thereby changing the electrical resistance. A resulting pulse change in resistance is detected. The pulses are counted while the fixed quantity of the mixture is drawn through the minute hole to indicate the amount of blood component particles in the mixture. The amount of hemoglobin (red pigment) in the mixture is measured with a colorimeter.

When the number of leucocytes and the amount of hemoglobin is measured by conventional apparatus using a test mixture containing hemolysed (disassociated) red blood corpuscles, two separate liquid routes: one for measuring the number of leucocytes, the other for measuring the amount of hemoglobin.

Therefore, the liquid routes of conventional devices are complicated and expensive.

In addition, conventional devices require large amounts of test mixture and a large amount of liquid for cleanup between tests.

Furthermore, testing of blood components is frequently done in a series of tests of different blood samples. Purging of the equipment between tests is required. An automated technique for performing the tests and for performing the cleanup is desirable.

OBJECTS AND SUMMARY OF THE INVENTION

Accordingly, it is an object of the invention to provide an apparatus for counting particles which detects changes in the electrical resistance as a mixture of an electrolyte and blood components is drawn through a minute aperture.

It is a further object of the invention to provide an apparatus capable of measuring a total particle content of a mixture of an electrolyte and blood components, and a separate means for determining the amount of hemoglobin in the mixture.

It is a further object of the present invention to provide an apparatus with simplified routes and lower liquid consumption.

It is a still further object of the invention to provide an apparatus for automated measurement of a plurality of blood samples, including automatic valve actuation for routing the samples, and for purging the measuring equipment at the conclusion of each test.

Briefly stated, the present invention provides a particle detector for detecting particles of blood components in an electrolyte. A fixed quantity of the mixture of blood components and electrolyte is drawn through a minute hole. Electrodes inside and outside the detector pass an electric current through the minute hole. When a particle passes through the hole, it partially blocks the hole, whereby a sharp change is experienced in the amount of current passing through the electrolyte. A syringe fluid path in the detector enters the fluid path for the test fluid at right angles thereto. The inside electrode is disposed in the syringe fluid path near its junction with the fluid path for the test fluid. A colorimeter is placed in series with the flow of the test fluid to measure the concentration of hemoglobin in the test fluid. Automated control of the particle detector is provided by a plurality of cams driving a corresponding plurality of pistons. One of the pistons serves as a syringe for pumping test fluid during a test and for pumping purge fluid for cleanup prior to the next test. The remaining pistons, with interconnecting chambers, perform valve functions.

According to an embodiment of the invention, there is provided a particle detector for detecting particles in an electrolyte, comprising: a body, means for forming an aperture in the body, a fluid path in the body communicating with the aperture, a syringe liquid path in the body, the syringe liquid path terminating in the fluid path, a first electrode in the body, the first electrode being disposed in the syringe liquid path near a junction of the syringe liquid path with the fluid path, a second electrode external to the body, and means for preventing direct electrical conduction through the body, whereby electrical conduction between the first and second electrodes is constrained to flow in the electrolyte through the aperture.

According to a feature of the invention, there is provided a system for detecting particles in an electrolyte, comprising: a detector, an aperture in the detector, a liquid path in the detector communicating with the aperture, means for moving a predetermined fixed quantity of the electrolyte through the aperture and the liquid path, means for measuring an electrical resistance of the electrolyte through the aperture, a colorimeter in the liquid path, and the colorimeter being of a type effective for measuring a density of a color of the electrolyte passing therethrough.

According to a further feature of the invention, there is provided a detector for detecting particles in an electrolyte comprising: a body, a liquid path in the body, an aperture in the body, a cross bore in the body communicating with the aperture and the liquid path, a syringe liquid path in the body, the syringe liquid path intersecting the cross bore, generally at right angles, at a point intermediate the aperture and the liquid path, whereby fluid flow between the aperture and the liquid path passes the syringe liquid bore, generally at right angles, and an electrode in the syringe liquid path.

According to a still further feature of the invention, there is provided a control system for controlling liquid flow in a particle detector, comprising: a plurality of cams, means for concertedly rotating the plurality of cams, a plurality of pistons contacting the plurality of cams, at least one of the pistons being a syringe effective for displacing a fixed quantity of the liquid, and at least some of a remainder of the pistons being valves controlling a flow of the liquid displaced by the syringe.

The above, and other objects, features and advantages of the present invention will become apparent from the following description read in conjunction with the accompanying drawings, in which like reference numerals designate the same elements.

DESCRIPTION OF THE DRAWINGS

FIG. 1 is a schematic diagram of a system for measuring blood components according to the prior art.

FIG. 2 is a drawing of a particle detector according to an embodiment of the invention.

FIG. 5 is a schematic side view of the embodiment of the invention of FIG. 2 with the control system thereof shown in greater detail.

FIG. 6 is a longitudinal cross section of valve V2 of FIG. 5.

DETAILED DESCRIPTION OF PREFERRED EMBODIMENT

Figure 3:
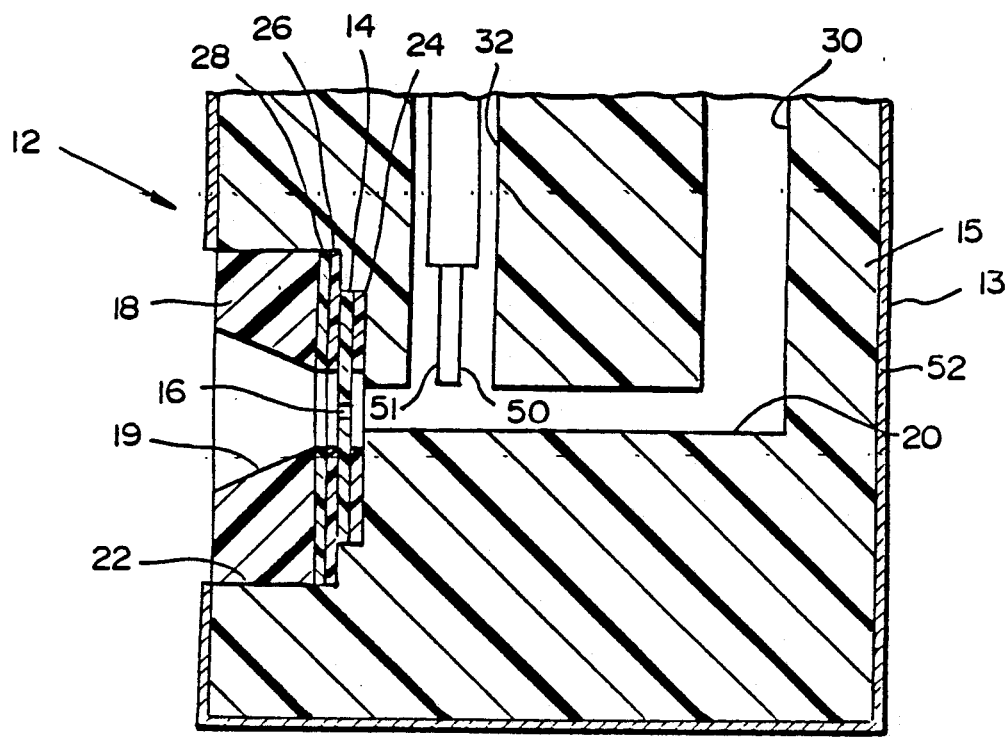
FIG. 3 is a cross section through a portion of the detector of FIG. 2.

Referring to FIG. 1, there is shown, generally at 45, relevant parts of a particle counting apparatus according to the prior art. One skilled in the art will understand that various valves and pumps may be necessary for the apparatus to operate. Such conventional items, since they not necessary to an understanding of the prior art, are omitted from the drawing and the description.

A particle detector 46 of the prior art is disposed in a container 60. A test liquid 58 partially fills container 60. A minute hole 48 in particle detector 46 is disposed below the level of test liquid 58. A first electrode 50 is disposed inside detector 46. A second electrode 52 is disposed in the space between the outside of detector 46 and the inside of container 60. A detector 62 is connected to electrode 50 and electrode 52. Particle detector 46 is made of an electrical non-conductor.

A fixed quantity apparatus 64 is connected through a pipe 54 to the interior of particle detector 46. A waste fluid container 70 receives waste fluid from particle detector 46. A diluting liquid tub 68 contains a supply of liquid for flushing particle detector 46 between tests, and for use during a test. The liquid in diluting liquid tub 68 is an electrically conducting electrolyte such as, for example, a saline solution.

A colorimeter 66 includes a pipe 56. Colorimeter 66 also has connections to diluting liquid tub 68 waste fluid container 70 for purging between tests.

The interior of particle detector 46 is filled with electrolyte, initially without the admixture of the blood sample. Test liquid 58 contains a sample of blood diluted with an electrolyte. The two electrolyte are preferably the same.

In operation, a current is passed between electrodes 50 and 52. Since particle detector 46 is made of a non-conducting material, the only path for electric current between electrodes 50 and 52 is through the electrolyte in minute hole 48. A fixed amount of the test liquid is drawn into detector 46 through minute hole 48 by fixed quantity device 64. The particles in the blood sample have a different electrical resistance than the electrolyte. As a particle passes through minute hole 48, it partly blocks minute hole 48, thereby changing the electrical resistance between electrodes 50 and 52. The resulting rapid changes produce pulse-type signals that are counted in detector 62 to measure the total number of particles in the fixed quantity of liquid drawn through minute hole 48.

To measure the concentration of hemoglobin, a sample of the test liquid is drawn into pipe 56 of colorimeter 66. The amount of hemoglobin is determined by the density of its characteristic red color. The apparatus of the prior art is capable of measuring hemolysed leucocytes and hemoglobin or, alternatively, it may be used to measure unhemolysed red blood cells.

For measuring hemolysed leucocytes and hemoglobin, a test liquid is prepared by diluting a blood sample 250-500 times using a suitable electrolyte fluid and adding drops of a hemolytic solvent to release the hemoglobin from the erythrocytes. The resulting test liquid contains particles of white blood corpuscles and hemolysed hemoglobin.

For measuring unhemolysed red blood corpuscles or blood times platelet (trombocytes), unhemolysed blood is diluted about 62,500 times before operating the apparatus of FIG. 1.

On completion of a test, the insides of particle detector 46 and colorimeter 66 are flushed with the diluting fluid. The waste fluid flows into waste liquid container 70.

Because of the difference in particle size between blood platelets and the particles existing in a hemolysed sample, the diameter of minute hole 48 may be changed so that the amount of blocking of electric current therethrough is adjusted to give an easily sensed signal. For a hemolysed blood sample, a diameter of about 100 microns gives a suitable change in electrical resistance as the particles of interest pass therethrough. A larger diameter for minute hole 48 may be desirable for measuring the number of unhemolysed blood platelets.

One of the problems with the prior-art device of FIG. 1 is the large volume of liquid contained in particle detector 46. On completion of each test, this large volume must be replaced from diluting liquid tub 68. In a laboratory doing serial testing of blood samples, this large usage may be a problem. A further problem arises from the use of separate fluid paths for particle counting and hemoglobin measurement. This adds to cost, and further increases the amount of flushing fluid required between tests. Referring now to FIG. 2, there is shown, generally at 10, a particle detector according to an embodiment of the present invention. A detector 12 is disposed in a container 38 containing a test liquid path 30. An outside electrode 13 is disposed in test liquid 36 outside detector 12. An aperture plate 14, having minute hole 16 therein, is located near the bottom of the detector 12. A syringe liquid path 32 provides access to detector 12 for flushing electrolyte used between tests. A test liquid path 30 permits passage of the test mixture that has passed through aperture plate 14 to be drawn from syringe liquid path 32.

A fixed quantity apparatus 64 draws a fixed quantity of the test mixture through aperture plate 14 and test liquid path 30. A colorimeter 40 is disposed in series with the intake path of fixed quantity apparatus 64. A diluting fluid container 44 provides a supply of clean electrolyte for use during operation of the apparatus. A waste fluid tub 42 receives spent electrolyte. A plurality of valves V1, V2, V3 and V4 control the cyclic operation of particle detector 10, as will be explained hereinafter. An insulating chamber 41 is disposed in the line between waste fluid tub 42 and fixed quantity apparatus 64. Similarly, an insulating chamber 43 is disposed in the line from diluting fluid container 44. Insulating chambers 41 and 43 reduce the entry of electrical noise and mechanical vibration into the apparatus.

Referring now to FIG. 3, detector 12 includes a solid body 15 in which test liquid path 30 and syringe liquid path 32 are bored. A cross bore 20 intercepts the ends of test liquid path 30 and syringe liquid path 32 and leads to minute hole 16. Syringe liquid path 32 joins cross bore 20 generally at right angles to the flow of liquid between minute hole 16 and test liquid path 30. An electrode 50 is disposed in syringe liquid path 32 with its end 51 closely adjacent the junction of syringe liquid path 32 and cross bore 20.

Minute hole 16 is formed in an aperture plate 14 that is secured in a stepped opening 22 aligned with cross bore 20. A gasket 24 behind aperture plate 14 and a further gasket 26 in front of aperture plate 14 are squeezed into a fluid-tight condition by a threaded ring 18 threaded into stepped opening 22. Optionally, a ring 28 of a low-friction material such as, for example, Teflon, may be interposed between gasket 26 and threaded ring 18 to ease installation and removal of aperture plate 14. A conical hole 19 leads from minute hole 16 to the exterior of detector 12.

Electrode 52 may be located anywhere in the test fluid outside detector 12, as indicated in the prior-art device of FIG. 1. In the preferred embodiment, however, electrode 52 is a electrically conductive film 13 coated directly on the exterior surface of detector 12. This provides a compact assembly requiring fewer parts which are more easily assembled.

In operation, detector 12 is used in a similar manner to that described for the prior-art device of FIG. 1 except that an electric current passes between electrode 50, in syringe liquid path 32, and electrically conductive film 13 on the outer surface of detector 12. In this path, the electric current passes through minute hole 16.

Although not shown in FIGS. 2 and 3, it will be understood that electrode 50 and electrically conductive film 13 are connected to a detector, wherein pulses of current change produced by passage of particles through minute hole 16 are detected, as in the prior-art device.

It is of note, however, that electrode 50 is disposed in syringe liquid path 32 very close to the path of the incoming test fluid just after it has passed through minute hole 16. After passing electrode 50, the test fluid flows through test liquid path 30 and thence through colorimeter 40 (FIG. 2) on its way to fixed quantity apparatus 64 and waste fluid tub 42. The placement of electrode 50 out of the direct flow path of test fluid ensures that electrode 50 avoids contamination by the test fluid. Also, any contamination such as, for example, dust, protein and bubbles, that does reach electrode 50 is flushed away by the fluid injected through syringe liquid path 32 between tests. These factors permit detector 12 to provide stable readings and to retain sensitivity over a long period without disassembly for cleaning of electrode 50.

Detector 12 is made of an electrically insulating material that is resistant to chemicals. One example of such material is an ABS plastic.

Electrically conductive film 13 may be of any convenient material having the required electrical conductivity and resistance to chemicals. One suitable material is plated chromium. Electrode 50 is also preferably made of platinum.

The provision of electrically conductive film 13 on detector 12 tends to reduce electrical noise in the measurement.

Referring again to FIG. 2, after passing through test liquid path 30, the test liquid passes through colorimeter 40 wherein the amount of hemoglobin is measured by conventional colorimetric techniques.

On completion of a test, and before performing the next test, the test liquid is purged from the inner side of aperture plate 14, cross bore 20, liquid path 30 and calorimeter 40 by fluid from diluting fluid container 44 injected through syringe liquid path 32.

Figure 4:
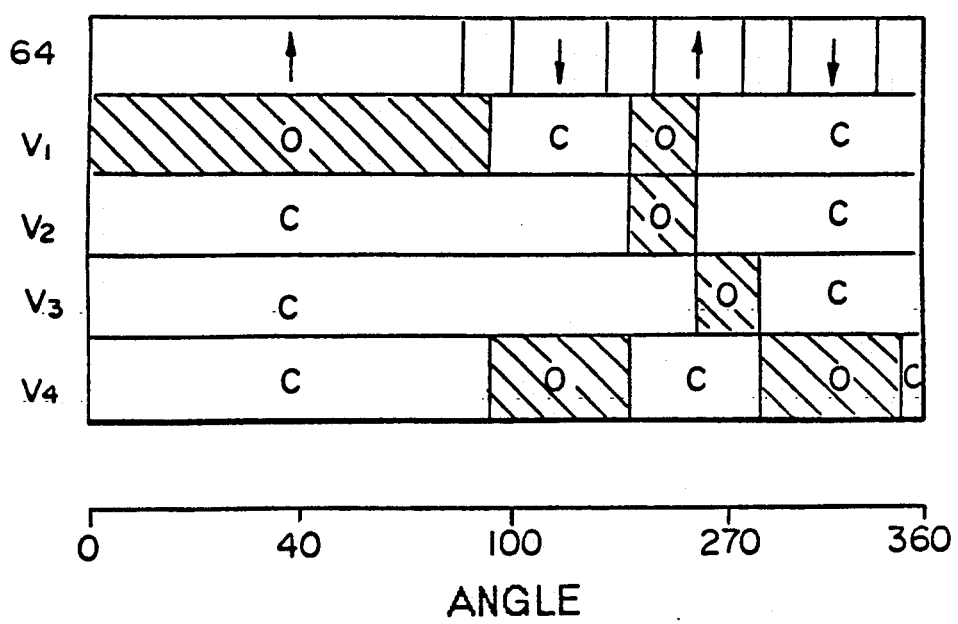
FIG. 4 is a sequence diagram to which reference will be made in describing the sequence of operations of the embodiment of FIG. 2.

Referring now to FIG. 4, a sequence diagram shows the sequence for fixed quantity apparatus 64 and valves V1-V4. The bottom axis divides a complete cycle into 360 degrees. An up arrow indicates intake by fixed quantity apparatus 64. A down arrow indicates output from fixed quantity apparatus 64. "O" means that a valve V is open. "C" means that a valve V is closed. Hatching emphasizes times that valves are open. V2-V4

Over the first 170 degrees valve V1 is opened and valves V2-V4 are closed. From 0 to about 160 degrees, fixed quantity apparatus 64 takes in a fixed quantity of the test liquid such as, for example, about 500-1000 ml. The test liquid passes through minute hole 16, cross bore 20, test liquid path 30 and colorimeter 40. During this time, particle detection and hemoglobin measurement is performed.

At about 170 degrees, valve V1 is closed and valve V4 is opened. The remaining valves remain closed.

From about 180 to about 215 degrees, fixed quantity apparatus 64 expels the liquid therein through V4 into waste fluid tub 42.

At about 225 degrees, valve V4 is closed, and valves V1 and V2 are opened.

From about 235 degrees to about 260 degrees, fixed quantity apparatus 64 draw in fluid from diluting fluid container 44, through valve V2, syringe liquid path 32, test liquid path 30, valve V1 and colorimeter 40.

At about 260 degrees, valves V1 and V2 are closed, and valve V3 is opened. Fixed quantity apparatus 64 continues drawing in fluid from diluting fluid container 44 until about 280 degrees, but the fluid during this period flows through valve V3, directly to colorimeter 40 and then to fixed quantity apparatus 64. This helps flush colorimeter 40 to prevent holdover contamination from the preceding test. It also fills colorimeter 40 with clean fluid so that colorimeter 40 may perform a baseline measurement of light transmission in preparation for the next test.

At about 290 degrees, valve V3 is closed and valve V4 is opened. All other valves remain closed. From about 300 to about 350 degrees, fixed quantity apparatus 64 expels the liquid drawn in during the preceding period to waste fluid tub 42.

At 360 degrees, a new cycle begins.

Referring now to FIG. 5, a control system for performing the functions of fixed quantity apparatus 64 and valves V1-V4 is shown, generally at 11.

A motor 106 is affixed to a supporter 114 by a fixture 108. A shaft 100 is rotatably held in supporter 114 by bearings 102 and 104. Shaft 100 is connected to shaft 110 of motor 106 by a connector 112. A plurality of cams K1-K5 are affixed to rotate with shaft 100. A plurality of correspondingly suffixed pistons P1-P5 contact the peripheral surfaces of cams K1-K5. Pistons P1-P5 are fitted into similarly suffixed cylinders in mating cylinder blocks 116 and 118, where they are constrained to move in straight paths, upward and downward in the figure.

Supporter 114 includes five stepped openings through which pass portions of pistons P1-P5. Correspondingly suffixed springs S1-S5 in the five openings provide resilient upward bearing force urging pistons P1-P5 into contact with cams K1-K5.

Cylinder blocks 116 and 118 are positioned on the lower part of supporter 114. Cylinder block 116 includes cavities A1-A5 into which pistons P1-P5 are fitted. Cylinder block 118 contains further cavities B1-B5.

Valve V2 consists of piston P1 and cavities A1 and B1. Valve V3 is formed by piston P2 and cavities A2 and B2. Valve V1 is formed by piston P3 and cavities A3 and B3. Fixed quantity apparatus 64 consists of piston P4 and cavities A4 and B4. Valve V4 consists of piston P5 and cavities A5 and B5.

Referring now to FIG. 6 an O-ring at the junction of supporter 114 and cylinder block 116 seals against the piston P1. A second O-ring at the junction of cylinder blocks 116 and 118 seal against piston P1 to form a sealable chamber A1 between itself and O-ring E1. A path T11 enters the sealable chamber A1 through cylinder block 116. Chamber B1, below O-ring F1 is joined by a path T12.

When piston P1 is in the lowered (closed) position shown, O-ring F1 prevents liquid communication between paths T11 and T12. When piston P1 is raised so that its peripheral surface is out of contact with O-ring F1, liquid communication between paths T11 and T12 is enabled.

Valves V1, V3 and V4 consist of similar elements.

A cycle of operation of particle detector 10 is completed during one complete revolution of cams K1-K5. Thus, the angular reference on the horizontal axis of FIG. 4 corresponds to the degrees of rotation of cams K1-K5 revolve.

One skilled in the art, with the present disclosure for reference, would be fully enabled to define the shapes of cams K1-K5 to perform the valve and fluid-displacement functions described herein. Thus, further description of the shapes of cams K1-K5 is omitted herefrom.

The apparatus for measuring the test liquid of the present invention has a number of advantages in comparison with prior art devices. It can be miniaturized and its cost may be less because the fluid route for counting the particles is also used for measuring the amount of pigment. The fluid circuit of the present invention is also simpler than the prior art.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

I claim:

1. A particle detector for detecting particles in an electrolyte, comprising:
   a body;
   means for forming an aperture in said body;
   a fluid path in said body communicating with said aperture;
   a syringe liquid path in said body communicating with said aperture;
   said syringe liquid path terminating in said fluid path;
   a first electrode in said body;
   said first electrode being disposed in said syringe liquid path near a junction of said syringe liquid path with said fluid path;
   a second electrode external to said body;
   a colorimeter in series flow with said fluid path; and
   means for preventing direct electrical conduction through said body, whereby electrical conduction between said first and second electrodes is constrained to flow in said electrolyte through said aperture.

2. A particle detector for detecting particles in an electrolyte, comprising:
   a body;
   means for forming an aperture in said body;
   a fluid path in said body communicating with said aperture;
   a syringe liquid path in said body;
   said syringe liquid path terminating in said fluid path;
   a first electrode in said body;
   said first electrode being disposed in said syringe liquid path near a junction of said syringe liquid path with said fluid path;
   a second electrode external to said body; and
   means for preventing direct electrical conduction through said body, whereby electrical conduction between said first and second electrodes is constrained to flow in said electrolyte through said aperture;
   said second electrode being disposed on an external surface of said body.

3. A particle detector according to claim 2, wherein said second electrode is a metallic layer plated on said external surface.

4. A particle detector according to claim 3, wherein said metallic layer is chromium.

5. A system for detecting particles in an electrolyte, comprising:
   a detector;
   an aperture in said detector;
   a liquid path in said detector communicating with said aperture;
   a syringe liquid path in said detector communicating with said aperture;
   said syringe liquid path terminating in said liquid path;
   means for moving a predetermined fixed quantity of said electrolyte through said aperture and said liquid path;
   means for measuring an electrical resistance of said electrolyte through said aperture;
   a colorimeter in said liquid path; and
   said colorimeter being of a type effective for measuring a density of a color of said electrolyte passing therethrough.

6. A detector for detecting particles in an electrolyte comprising:
   a body;
   a liquid path in said body;
   an aperture in said body;
   a cross bore in said body communicating with said aperture and said liquid path;
   a syringe liquid path in said body;
   said syringe liquid path intersecting said cross bore, generally at right angles, at a point intermediate said aperture and said liquid path, whereby fluid flow between said aperture and said liquid path passes said syringe liquid bore, generally at right angles; and
   an electrode in said syringe liquid path.

7. A detector according to claim 6, further comprising:
   a second electrode external to said body; and
   said second electrode being a metallic coating affixed to an external surface of said body.

* * * * *